US00PP24458P2

(12) United States Plant Patent
Blom

(10) Patent No.: US PP24,458 P2
(45) Date of Patent: May 13, 2014

(54) ***ECHINACEA* PLANT NAMED 'BUTTERFLY KISSES'**

(50) Latin Name: *Echinacea purpurea*
Varietal Denomination: Butterfly Kisses

(75) Inventor: Arie Blom, Oudewater (NL)

(73) Assignee: AB-Kwekersrechten, Zuidwolde (NL)

( * ) Notice: Subject to any disclaimer, the term of this patent is extended or adjusted under 35 U.S.C. 154(b) by 82 days.

(21) Appl. No.: 13/573,293

(22) Filed: Sep. 7, 2012

(51) Int. Cl.
*A01H 5/00* (2006.01)

(52) U.S. Cl.
USPC ..... Plt./428

(58) Field of Classification Search
USPC ..... Plt./428
See application file for complete search history.

*Primary Examiner* — Susan McCormick Ewoldt
(74) *Attorney, Agent, or Firm* — Penny J. Aguirre

(57) ABSTRACT

A new cultivar of *Echinacea purpurea*, 'Butterfly Kisses', characterized by its dwarf and compact plant habit, its well-branched strong stems, its floriferous habit, and its anemone-type composite inflorescences with ray florets that light red-purple and disk florets that are deeper red-purple.

2 Drawing Sheets

Botanical classification: *Echinacea purpurea.*
Variety denomination: 'Butterfly Kisses'.

BACKGROUND OF THE INVENTION

The present invention relates to a new and distinct cultivar of *Echinacea purpurea* and will be referred to hereafter by its cultivar name, 'Butterfly Kisses'. 'Butterfly Kisses' represents a new coneflower, an herbaceous perennial grown for landscape use.

The new cultivar arose from an ongoing breeding program of the Inventor's in Zuidwolde, The Netherlands. The objective of the breeding program is to develop new cultivars of anemone type *Echinacea* with very compact plant habits. The new cultivar arose from open pollination of an unnamed plant from the Inventor's breeding, designated as Ec 637-01, in summer of 2007. The male parent is unknown. 'Butterfly Kisses' was selected as a single unique plant from the resulting seedlings in July of 2009.

Asexual reproduction of the new cultivar was first accomplished by in vitro propagation in Heerhugowaard, The Netherlands in April of 2010 under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Butterfly Kisses' as a unique cultivar of *Echinacea.*

1. 'Butterfly Kisses' exhibits a dwarf and compact plant habit.
2. 'Butterfly Kisses' exhibits well-branched strong stems.
3. 'Butterfly Kisses' exhibits anemone-type composite inflorescences.
4. 'Butterfly Kisses' exhibits inflorescences with ray florets that light red-purple and disk florets that are deeper red-purple.
5. 'Butterfly Kisses' is very floriferous.

The female parent, designated as Ec 637-01, differs from 'Butterfly Kisses' in having an even more dwarf plant habit, in having weaker stems, and in having less branching. The new cultivar can be most closely compared to the cultivars 'Pink Double Delight' (U.S. Plant Pat. No. 18,803) and 'Pink Sorbet' (U.S. Plant Pat. No. 18,817). Both are similar to 'Butterfly Kisses' in having anemone type inflorescences that are pink in color. 'Pink Double Delight' differs from 'Butterfly Kisses' in having inflorescences with less contrast in color between the ray and disk florets and in having weaker, taller and less branched stems. 'Pink Sorbet' differs from 'Butterfly Kisses' in having larger flowers and in having taller and less branched stems.

BRIEF DESCRIPTION OF THE DRAWING

The plants in the accompanying photographs depict the characteristics of a two year-old plant of 'Butterfly Kisses' as field grown in Zuidwolde, The Netherlands and placed in a two-gallon container for the photographs.

The photograph in FIG. 1 provides a side view of a plant of 'Butterfly Kisses' in bloom.

Figure 1:
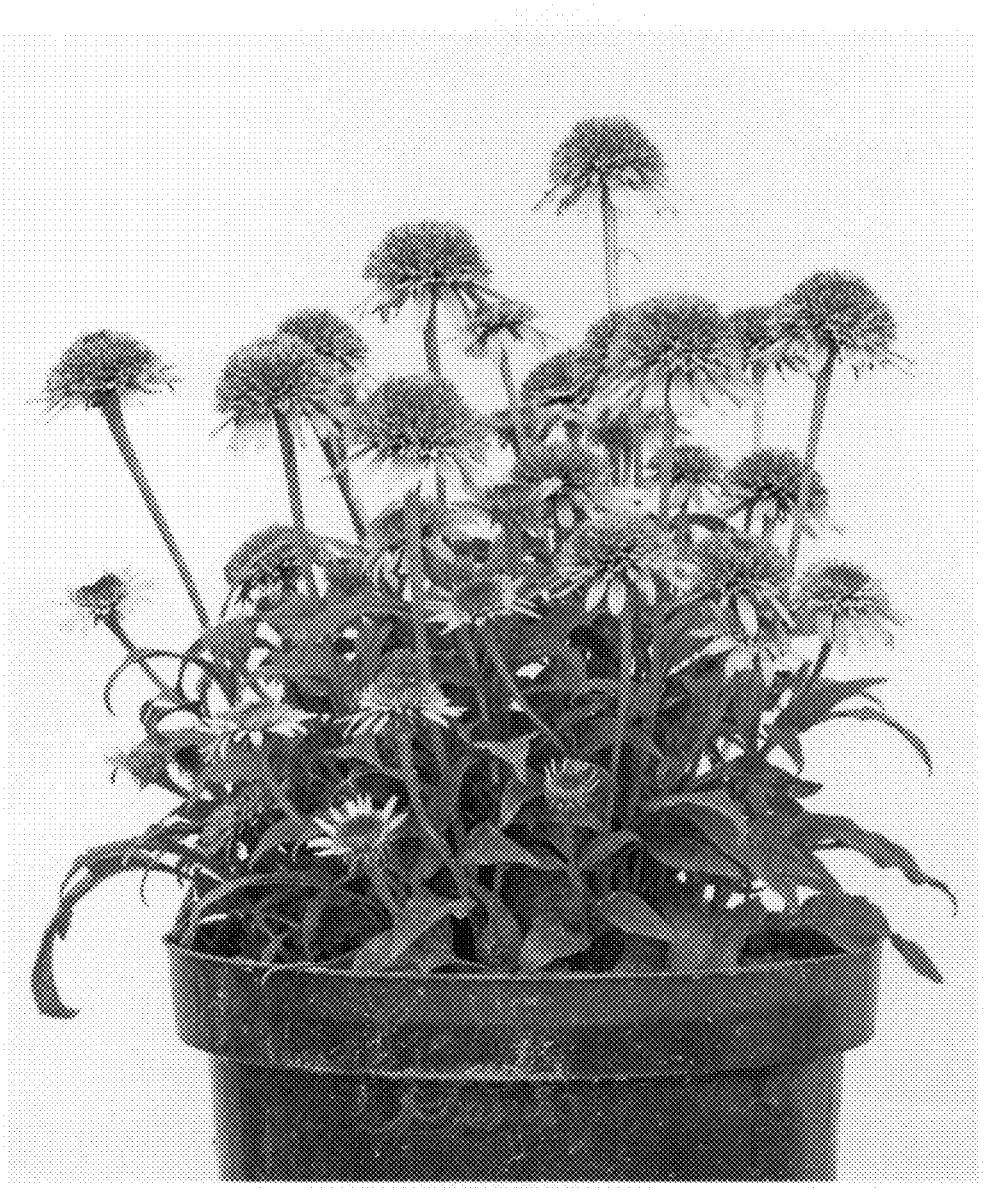
Figure 2:
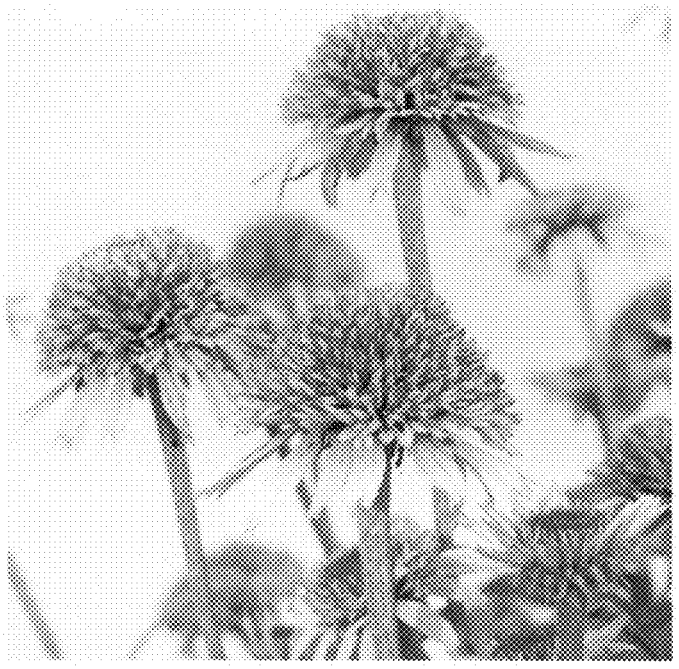

The photograph in FIG. 2 provides a close-up view of inflorescences of 'Butterfly Kisses'.

Figure 3:
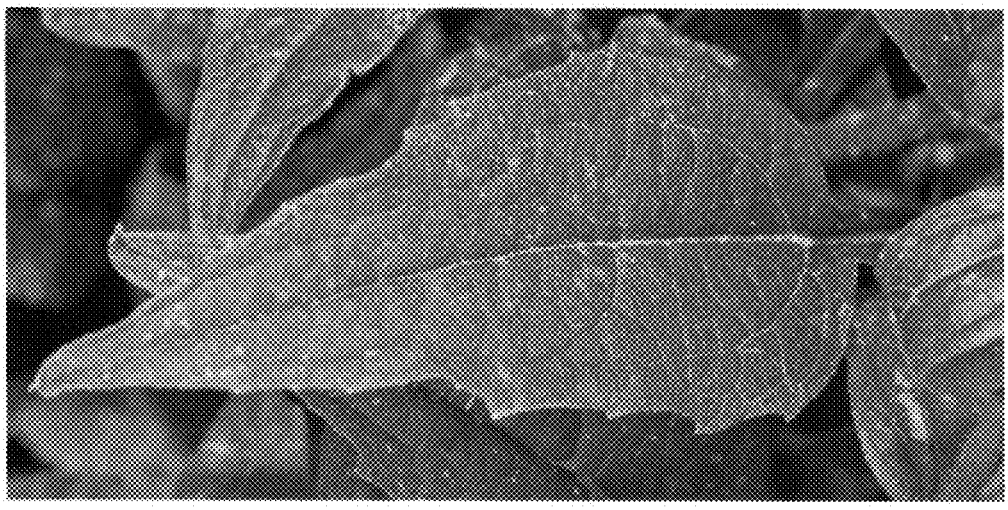

The photograph in FIG. 3 provides a close-up view of a leaf of 'Butterfly Kisses'. The colors in the photograph may differ slightly from the color values cited in the detailed botanical description, which accurately describe the colors of the new *Echinacea.*

BOTANICAL DESCRIPTION OF THE PLANT

The following is a detailed description of two year-old plants of the new cultivar as field grown in Zuidwolde, The Netherlands. Plants were grown under average day temperatures ranging from 16° to 28° C. and average night temperatures of 6° to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Continuously from mid July to mid-September in The Netherlands.

*Plant type*.—Herbaceous perennial.

*Plant habit*.—Clump forming, dwarf, compact.

*Height and spread*.—About 50 cm in height and spread.

*Cold hardiness*.—At least to U.S.D.A. Zone 4.

*Diseases and pests*.—No particular resistance or susceptibility to pests or diseases has been observed.

*Root description*.—Fibrous.

*Propagation*.—Tissue culture preferred.

*Growth rate*.—Moderate, approximately 8 cm per month in the spring.

Stem description:

*Shape*.—Rounded.

*Stem color*.—144A.

*Stem size*.—Average of 4 mm in diameter and an average of 19.7 cm in height.

*Stem surface*.—Moderately covered with short strigose hairs; 0.5 mm in length, NN155C to NN155D in color.

*Stem strength*.—Very strong.

*Stem aspect*.—Stems grow in an average angle of 15° from the base (0°=vertical).

*Stem number*.—Average of 2 main stems.

*Branching*.—21 lateral branches per main stem.

Foliage description:

*Leaf shape*.—Narrow ovate.

*Leaf division*.—Simple.

*Leaf base*.—Short attenuate.

*Leaf apex*.—Acute.

*Leaf venation*.—Pinnate, upper surface; 144C, lower surface; 145B to 145C.

*Leaf margins*.—Coarsely and shallow dentate-serrate.

*Leaf attachment*.—Petiolate.

*Leaf arrangement*.—Alternate.

*Internode length*.—An average of 3 cm.

*Leaf size*.—Average of 7.1 cm in length and 2.6 cm in width.

*Leaf color*.—Young upper surface; 137A to 137B, young lower surface; 138A, mature upper surface; N137A, mature lower surface; 137C.

*Leaf surface*.—Upper surface and lower surfaces slightly glossy and moderately covered with very short strigose hairs; average of 0.3 mm in length and 155D in color.

*Petioles*.—Upper stem leaves nearly sessile, average length of petioled leaves is 2.4 cm in length, v-shaped petiole is 2.5 mm in height and 2 mm in width, upper and lower surfaces smooth, upper surface color; 144C, margins N137B to N137C, lower surface color; 144B, margins N137A.

Flower description:

*Type*.—Terminal capitulum, heterogamous with ray florets around the head margin and anemone-type disk florets in the center.

*Capitulum number*.—One terminal capitulum per main stem and lateral branch.

*Lastingness of inflorescence*.—About 10 days.

*Capitulum size*.—Matures to about 3.8 cm in height and 6.3 cm in diameter, disk size is 4.5 cm in diameter.

*Fragrance*.—None.

*Involucral bracts or phyllary*.—About 48 arranged in 3 overlapping rows, up to 0.6 cm in length and 2 mm in width, dull in appearance, cuneate at base, acute apex, ovate in shape, entire margins moderately covered with short hairs 0.3 mm in length and 155D to in color, upper surface; smooth 143C in color, lower surface smooth and 137C in color.

*Buds*.—Flattened globular in shape with immature ray florets pointed upright, up to 2 cm in diameter and 2.5 cm in length, between 137C, immature ray florets 180D, tips 150D.

*Peduncle*.—Strong, straight on top of main (flowering) stem, average angle of secondary and tertiary peduncles 25° (0°=straight upright), strong in strength, 144C in color, moderately covered with short strigose hairs, average length of 1 mm and 155D in color, terminal peduncle is 11.6 cm in length and 3 mm in diameter, fourth peduncle is 6.9 cm in length and 3 mm in diameter, no seventh peduncle.

*Ray florets*.—Rotate, about 13, oblanceolate in shape, about 3 cm in length and 0.7 cm in width, praemorse to cleft apex, cuneate base, entire margin, moderately drooping in an average angle of −40°, upper and lower surface texture is smooth and ribbed lengthways (carinate), color: when opening upper surface; 61D, when opening lower surface; 59D, tip 145B, when fully opened upper surface; 186C, when fully opened lower surface; 59D, base and outer tip 146D, fading to on upper surface; 182C to 182D, fading to on lower surface; 182D, base and outer tip 146D.

*Disk flowers* (*bisexual*).—Numerous, about 260, campanulate with five ray floret-like petals shaped narrow oblong to narrow lanceolate, upper 30% free, about 1.1 cm in length and 5 mm in width, entire margin, lower 70% of each disc floret is fused, free tips acute, upper surface smooth, dull and slightly velvety in appearance, lower surface smooth and slightly glossy in appearance, color: upper surface when opening; 59D, lower surface when opening; 59D, upper surface when fully opened; 59D, lower surface when fully opened; 185C to 185D.

*Receptacle*.—Triangular in shape, about 0.6 cm in diameter and 1 cm in height, color is 155C.

*Receptacle spines*.—Average of 260, acicular in shape, acute apex, attenuate base, smooth and glossy surface, color: apex; 46A, mid-section; 17A, base; 144B to 144C.

Reproductive organs (only present in disc florets):

*Gynoecium*.—Pistil; 15 mm in length, style; 3 mm in length and 187D in color, ovary; 157D in color.

*Androcoecium*.—Stamens; 4, filament 2 mm in length and 199D in color, anther; narrow oblong in shape, 1 mm in length and 164D in color, no pollen detected.

*Fruit/seed*.—No fruit or seed detected to date.

It is claimed:

1. A new and distinct cultivar of *Echinacea* plant named 'Butterfly Kisses' substantially as herein illustrated and described.

* * * * *